(12) United States Patent
Rudser

(10) Patent No.: US 11,301,453 B2
(45) Date of Patent: Apr. 12, 2022

(54) CLINICAL DEVICE WITH DATA TRANSFER

(71) Applicant: HeartWare, Inc., Miami Lakes, FL (US)

(72) Inventor: John Rudser, Miami, FL (US)

(73) Assignee: HEARTWARE, INC., Miami Lakes, FL (US)

( * ) Notice: Subject to any disclaimer, the term of this patent is extended or adjusted under 35 U.S.C. 154(b) by 184 days.

(21) Appl. No.: 16/448,065

(22) Filed: Jun. 21, 2019

(65) Prior Publication Data

US 2019/0391970 A1 Dec. 26, 2019

Related U.S. Application Data

(60) Provisional application No. 62/689,370, filed on Jun. 25, 2018.

(51) Int. Cl.
*G06F 16/23* (2019.01)
*G06F 16/22* (2019.01)
*G01F 15/06* (2006.01)
*G01R 21/133* (2006.01)
(Continued)

(52) U.S. Cl.
CPC ...... *G06F 16/2365* (2019.01); *G06F 16/2228* (2019.01); *G01F 15/068* (2013.01); *G01R 21/133* (2013.01)

(58) Field of Classification Search
CPC ............. G06F 16/2365; G06F 16/2228; G01F 15/068; G01R 21/133; G16H 40/67; G16H 10/60
See application file for complete search history.

(56) References Cited

U.S. PATENT DOCUMENTS 9,427,508 B2    8/2016 Reyes et al.
2011/0169644 A1*    7/2011 Muhsin ............... G08B 25/008
                                                            340/573.1
2012/0245681 A1    9/2012 Casas et al.
(Continued)

OTHER PUBLICATIONS

International Search Report and Written Opinion dated Sep. 30, 2019, for corresponding International Application No. PCT/US2019/038387; International Filing Date: Jun. 21, 2019, 11 pages.
(Continued)

*Primary Examiner* — Robert W Beausoliel, Jr.
*Assistant Examiner* — Mohammad Solaiman Bhuyan
(74) *Attorney, Agent, or Firm* — Shumaker & Sieffert, P.A.

(57) ABSTRACT

An automated method for evaluating completeness of clinical data being transferred from a clinical device. The clinical data includes continuously logged data, intermittently logged data, and timestamp data associated with each of the continuously logged data and intermittently logged data. The method is executed by a processor and includes receiving the clinical data from the clinical device and based on the timestamp data associated with the continuously logged data, determining a time span over which the continuously logged data was obtained. The timestamp data associated with the intermittently logged data is compared with the determined time span. If any timestamp data associated with the intermittently logged data does not occur within the determined time span, an alert is issued indicating that the continuously logged data of the clinical data is incomplete.

19 Claims, 5 Drawing Sheets

(51) Int. Cl.
*G16H 40/67* (2018.01)
*G16H 10/60* (2018.01)

(56) References Cited

U.S. PATENT DOCUMENTS

| | | | |
|---|---|---|---|
| 2013/0246089 A1* | 9/2013 | Gross | G16H 40/63 |
| | | | 705/2 |
| 2014/0100413 A1 | 4/2014 | Casas et al. | |
| 2015/0367048 A1 | 12/2015 | Brown et al. | |
| 2016/0166211 A1 | 6/2016 | Brown et al. | |
| 2016/0335409 A1* | 11/2016 | Mensinger | A61B 5/1495 |
| 2017/0119256 A1 | 5/2017 | Demou et al. | |
| 2017/0209632 A1* | 7/2017 | Pierce | A61M 60/50 |
| 2017/0224895 A1 | 8/2017 | Voskoboynikov et al. | |
| 2017/0246366 A1 | 8/2017 | Rudser | |
| 2018/0082036 A1* | 3/2018 | Hanrahan | G16H 50/20 |

OTHER PUBLICATIONS

International Search Report and Written Opinion of International Application No. PCT/US2019/038387, dated Sep. 30, 2019, 10 pp.
International Preliminary Report on Patentability from International Application No. PCT/US2019/038387, dated Dec. 29, 2020, 8 pp.
Response to Communication Pursuant to Rule 161/162 dated Feb. 2, 2021, from counterpart European Application No. 19735205.7, filed Jul. 14, 2021, 10 pp.

* cited by examiner

CLINICAL DEVICE WITH DATA TRANSFER

CROSS-REFERENCE TO RELATED APPLICATION

This application claims the benefit of U.S. Application Ser. No. 62/689,370, filed Jun. 25, 2018.

FIELD

The present technology is generally related to implantable blood pumps, and in particular, extracting data from an implantable blood pump and automatically analyzing completeness of the data.

BACKGROUND

Implantable blood pumps may be used to provide assistance to patients with late stage heart disease. Blood pumps operate by receiving blood from a patient's vascular system and impelling the blood back into the patient's vascular system. By adding momentum and pressure to the patient's blood flow, blood pumps may augment or replace the pumping action of the heart. For example, a blood pump may be configured as ventricular assist device or "VAD."

A VAD is a device which is used to assist the heart of a mammalian subject such as a human patient. A typical VAD includes a pump which is implanted in the body of the subject. The pump typically has an inlet connected to a source of blood to be circulated, and an outlet connected to an artery. Most typically, the inlet of the pump is connected to the interior of the left ventricle and the outlet of the pump is connected to the aorta, so that the pump operates in parallel with the left ventricle to impel blood into the aorta. The pump may be a miniature rotary impeller pump having an impeller disposed in a pump housing and driven in rotation by a small electric motor which may be closely integrated with the pump. The motor in turn typically is powered by an implantable power source such as a storage battery with an arrangement for charging the battery from an external power source. The VAD typically includes a control system which controls operation of the power source so as to drive the impeller at a set rotational speed and thus provide constant pumping action.

Patient health can be monitored using both patient-specific physiological data and pump operational data collected by the control system of the VAD. In some situations, the data collected by the VAD control system may be extracted and transmitted for analysis, such as to a central location in which data from several VADs is gathered and analyzed. Extracting clinical data from a VAD and sending it to another location generally involves connecting the VAD to a computer, extracting the data from the VAD control system onto the computer, and then transmitting the extracted data from the computer to another location.

If the VAD is disconnected from the computer before data extraction is completed, then the data sent out for analysis will be incomplete. To facilitate completeness of the transmitted data, a person must manually inspect the data. If the inspection occurs after the data has been transmitted over the network, and the data is discovered to be incomplete, then the person must request the data to be resent, thereby delaying analysis of the data.

SUMMARY

The techniques of this disclosure generally relate to extracting data from an implantable blood pump and automatically analyzing completeness of the data.

The present disclosure provides systems, devices, and methods for extracting data from a clinical device, and automatically analyzing completeness of the data. One example of a clinical device to which the principles of the present disclosure apply is a VAD. However, those skilled in the art will recognize that the same principles are applicable to other patient-specific clinical devices, such as, pacemakers, defibrillators, artificial hearts, or any other electronic device that may be implanted in or mounted on a patient and includes a control circuit capable of logging device-related and patient-related data.

In one aspect, the present disclosure provides an automated method for evaluating completeness of clinical data being transferred from a clinical device. The clinical data includes continuously logged data, intermittently logged data, and timestamp data associated with each of the continuously logged data and intermittently logged data. The method is executed by a processor and includes receiving the clinical data from the clinical device and based on the timestamp data associated with the continuously logged data, determining a time span over which the continuously logged data was obtained. The timestamp data associated with the intermittently logged data is compared with the determined time span. If any timestamp data associated with the intermittently logged data does not occur within the determined time span, an alert is issued indicating that the continuously logged data of the clinical data is incomplete.

In another aspect, receiving the clinical data from the clinical device comprises receiving the intermittently logged data before receiving the continuously logged data.

In another aspect, the continuously logged data comprises one or more operating parameters of the clinical device.

In another aspect, the clinical device is a blood pump, and wherein the operating parameters of the blood pump comprises one or more of a flow rate of blood exiting the pump, power supplied to the pump, and motor speed of the pump.

In another aspect, the intermittently logged data comprises at least one of: one or more logged events indicating a change in operation of the clinical device and one or more logged alarms indicating a detected adverse operating condition of the clinical device.

In another aspect, the clinical device is a blood pump, and wherein the intermittently logged data comprises at least one of: a low flow alarm; a suction condition alarm; a low battery alarm; and a power disconnection alarm.

In another aspect, the clinical data further comprises patient data and clinical device data that are not associated with a timestamp.

In another aspect, the clinical device is ventricular assist device or a blood pump.

In another aspect, the recited steps are performed at a location of the clinical device, and further comprising, if all timestamp data associated with the intermittently logged data occurs within the determined time span, transmitting the clinical data over a network to a remote destination.

In another aspect, the recited steps are performed at an originating location remote from the clinical device, and wherein the clinical data is received over a network connection from an originating location, and wherein the alert indicating that the continuously logged data of the clinical data is incomplete is transmitted over the network to the originating location.

In one aspect, the disclosure provides an apparatus for evaluating completeness of clinical data being transferred from a clinical device, the clinical data comprising continuously logged data, intermittently logged data, and timestamp data associated with each of the continuously logged data and intermittently logged data. The apparatus comprises memory storing instructions and a processor for executing the instructions stored in the memory. The apparatus is configured to receive the clinical data from the clinical device. The processor being configured to: based on the timestamp data associated with the received continuously logged data, determine a time span over which the continuously logged data was obtained; compare the timestamp data associated with the intermittently logged data with the determined time span. If any timestamp data associated with the intermittently logged data does not occur within the determined time span an alert indicating that the continuously logged data of the clinical data is incomplete is issued.

In another aspect, the processor is configured to determine whether the intermittently logged data is received before the continuously logged data.

In another aspect, the clinical device is a blood pump, and wherein the operating parameters of the blood pump comprises one or more of a flow rate of blood exiting the pump, power supplied to the pump, and motor speed of the pump.

In another aspect, the intermittently logged data comprises at least one of one or more logged events indicating a change in operation of the clinical device and one or more logged alarms indicating a detected adverse operating condition of the clinical device.

In another aspect, the clinical device is a blood pump, and wherein the intermittently logged data comprises at least one of: a low flow alarm; a suction condition alarm; a low battery alarm; and a power disconnection alarm.

In another aspect, the clinical data further comprises patient data and clinical device data that are not associated with a timestamp.

In another aspect, the apparatus is located in proximity to the clinical device, and the processor is further configured to, if all timestamp data associated with the intermittently logged data occurs within the determined time span, transmit the clinical data over a network to a remote destination.

In another aspect, the apparatus is located remote from the clinical device, and wherein the apparatus receives the clinical data over a network connection from an originating location, and wherein the processor is further operable to transmit the alert indicating that the continuously logged data of the clinical data is incomplete over the network to the originating location.

In one aspect, the disclosure provides an apparatus for evaluating completeness of clinical data being transferred from a ventricular assist device, the clinical data comprising continuously logged data including one or more operating parameters of the ventricular assist device, intermittently logged data, and timestamp data associated with each of the continuously logged data and intermittently logged data. The apparatus comprises memory storing instructions and a processor for executing the instructions stored in the memory. The apparatus is configured to receive the clinical data from the ventricular assist device. The processor being configured to: based on the timestamp data associated with the received continuously logged data transferred from the ventricular assist device, determine a time span over which the continuously logged data was obtained; determine whether the intermittently logged data is received before continuously logged data; compare the timestamp data associated with the intermittently logged data with the determined time span. If any timestamp data associated with the intermittently logged data does not occur within the determined time span an alert indicating that the continuously logged data of the clinical data is incomplete is issued.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
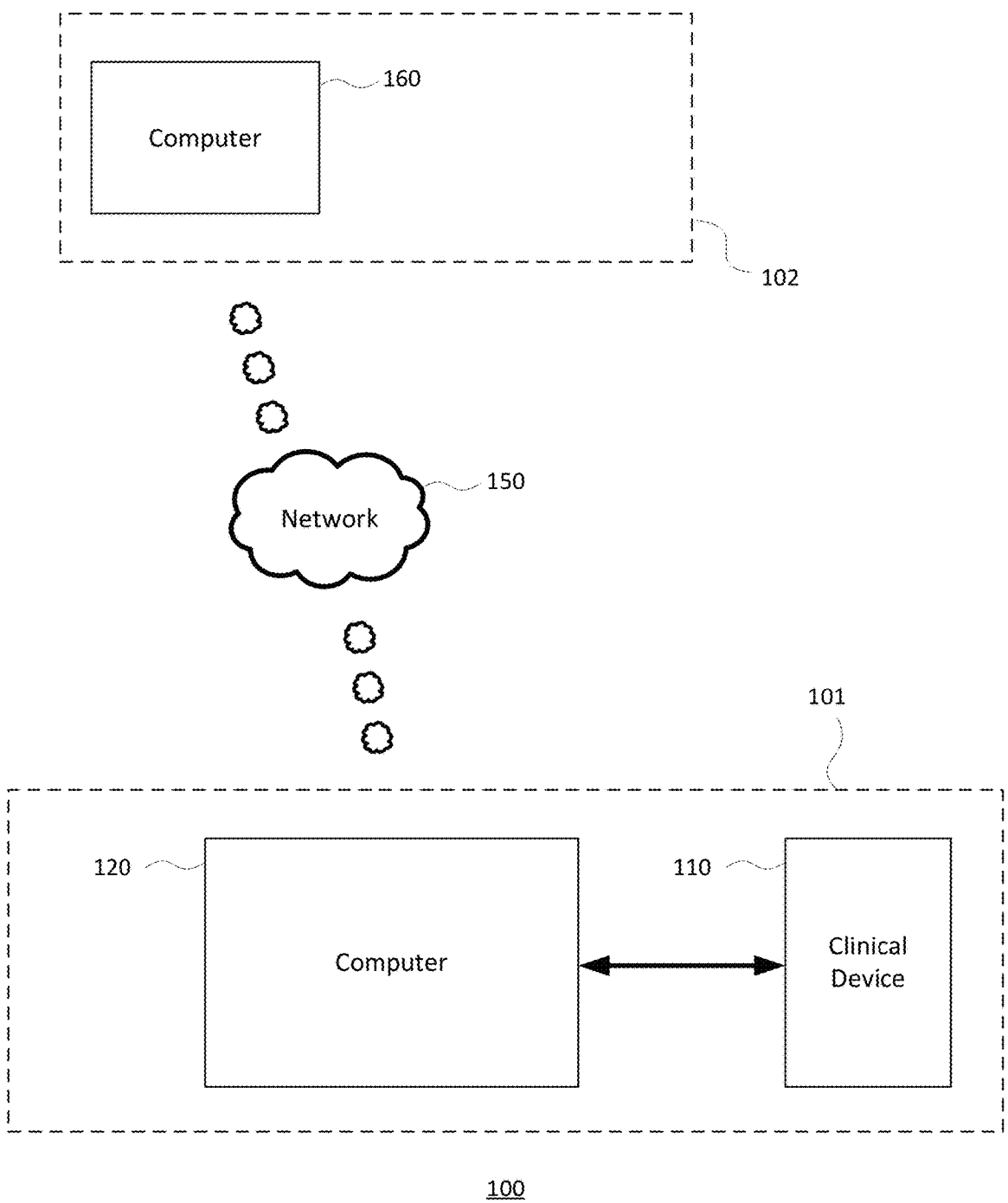
FIG. 1 is an exemplary system for extracting data from a clinical device for analysis construction in accordance with the principles of the present application.

FIG. 1 shows an example system 100 for extracting data from a clinical device 110 (e.g., a blood pump, VAD, or other implantable medical devices) for analysis. In the example of FIG. 1, the patient occasionally brings the clinical device to a local clinical facility 101 that is convenient for the patient to visit. At the clinical facility 101, data is extracted from the patient's clinical device 110, and sent out to a remote location 102 for analysis. The remote location may be a headquarters, manufacturing facility, or research and development facility for the clinical device maker, or any other facility at which the clinical device is manufactured, tested, or otherwise analyzed. Other patients may similarly bring their clinical devices to other clinical facilities (not shown), so that the data from their clinical devices may be extracted and sent out to the same remote location 102 for analysis.

At the clinical facility 101, the clinical device 110 is connected to a computer 120 or other network-coupled apparatus. The connection may be wired or wireless. A command may be provided from either the clinical device 110 or from the computer 120, which may further be provided by a secure comminutions channel in order to initiate extraction of the data from the clinical device 110 to the computer 120. The clinical facility computer 120 is connected to a computer 160 (or other network coupled apparatus) at the remote location 102 over a network 150. The file extracted from the clinical device 110 may be transmitted between the computers 120, 160 over the network 150 for further analysis.

Because visiting the clinical facility 101 is relatively convenient for the patient (at least as compared to visiting the remote location), data may be extracted from the clinical device 110 on a relatively regular basis, such as on any occasion when the patient visits a clinical facility, on a regularly scheduled basis, or when the patient experiences a health event that warrants further examination (e.g., the patient experiences an adverse health condition, the device has an operational malfunction, etc.).

Figure 2:
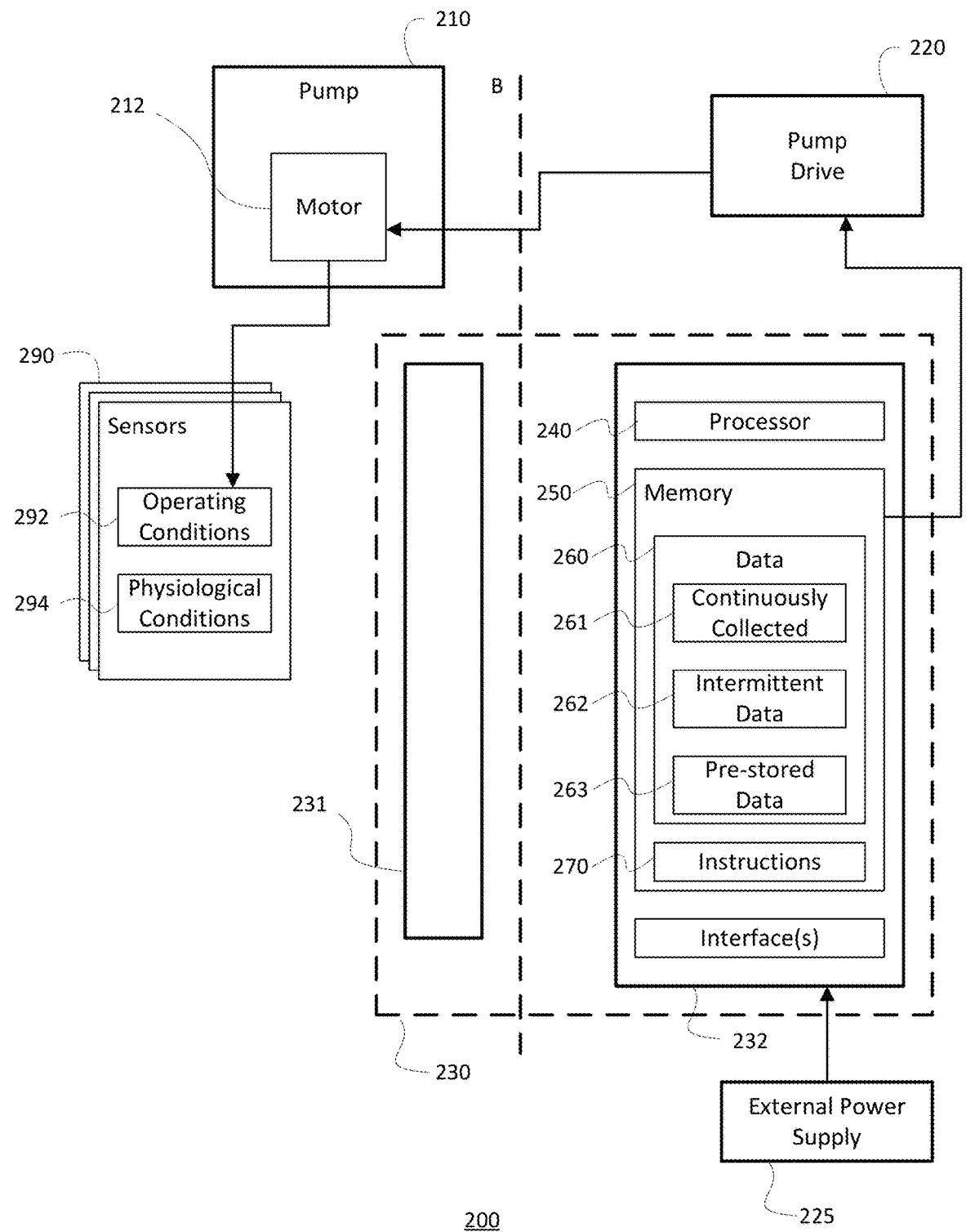
FIG. 2 is a block diagram of an example VAD clinical device shown in FIG. 1.

FIG. 2 is a block diagram of an example VAD clinical device 200. In the example of FIG. 2, the VAD 200 includes a pump 210, a drive circuit 220, and a motor 212 for driving an impeller of the pump at a rotational speed prescribed by the drive circuit by means of a motor commutation technique. The VAD, like other clinical devices, further includes one or more control circuits 230 for controlling operation (e.g., of the drive circuit and motor), for logging operational data, and for logging physiological data of the patient. The control and data collection functions of the one or more controllers may be divided between an implanted controller 231 and an external controller 232. For example, the implanted controller may be primarily responsible for controlling operation of the motor 212, whereas the external controller may include larger memory storage and be primarily responsible for long-term storage of collected data, at least until the data is extracted. If multiple control circuits are used, the control circuits may be capable of communicating between one another over a wired communication channel (one or more wires, USB cable, Ethernet cable) or a wireless connection (e.g., Bluetooth, MICS, NFC, RFID wireless network). For purposes of clarity, the one or more control circuits are referred to herein collectively as a "control circuit." Similarly, the control circuit(s) may include either or both of multiple processors and memory devices, which are also referred to herein as a "processor" 240 and "memory" 250.

The memory 250 stores information accessible by processor 240 including instructions 270 for execution by the processor 240 and data 260 which is retrieved, manipulated or stored by the processor 240. Data 260 may include data received from one or a combination of the sensors 290 connected to the control circuit 230. By way of example, such data may include continuously collected data 261 (e.g., flow rate, differential pressure, pump speed, back electromotive force (BEMF), etc.) intermittent data 262 (e.g., suction or low flow alarms, low battery or battery disconnect alarms, etc.) and pre-stored data 263 (e.g., patient information, pump information). The instructions 270 may include one or more modules for analyzing or processing the data 260, such as detecting low flow conditions, detecting suction or occlusion conditions, detecting low battery conditions, detecting battery disconnect conditions, etc. Some such modules are described in the following commonly owned patents and applications: U.S. Pat. No. 9,427,508; U.S. application Ser. No. 13/951,302; U.S. application Ser. No. 14/743,166; U.S. Provisional Application Ser. No. 62/249,601; U.S. Provisional Application Ser. No. 62/299,747. The disclosures of those applications are hereby incorporated by reference in their entireties.

An external power source 225 or sources may be connected to the VAD 200 to supply power to the control circuit 230 and the drive circuit 220. Additionally, one or more batteries (e.g., implanted battery, external battery) may be included in the VAD 200 to store power and supply stored power to the VAD components when the external power supply 225 is disconnected.

One or more communication interfaces 280 for transmitting stored data 260 may also be included. The interfaces 280 may include either or both wired and wireless connections. Extraction of data from the VAD, as described herein, may be performed over the interface 280. Collection of data from one or more sensors 290 connected to the VAD may also be performed over the interface 280. The sensors 290 may monitor one or more operating conditions 292 of the pump 210 (e.g., motor speed, phase, angular position, pressure, back electromotive force, power supplied to motor, etc.) and physiological conditions 294 of the patient (e.g., atrial pressure, heart rate, etc.). Data collected from the sensors may be stored in memory 250, for instance in a log file.

Figure 3:
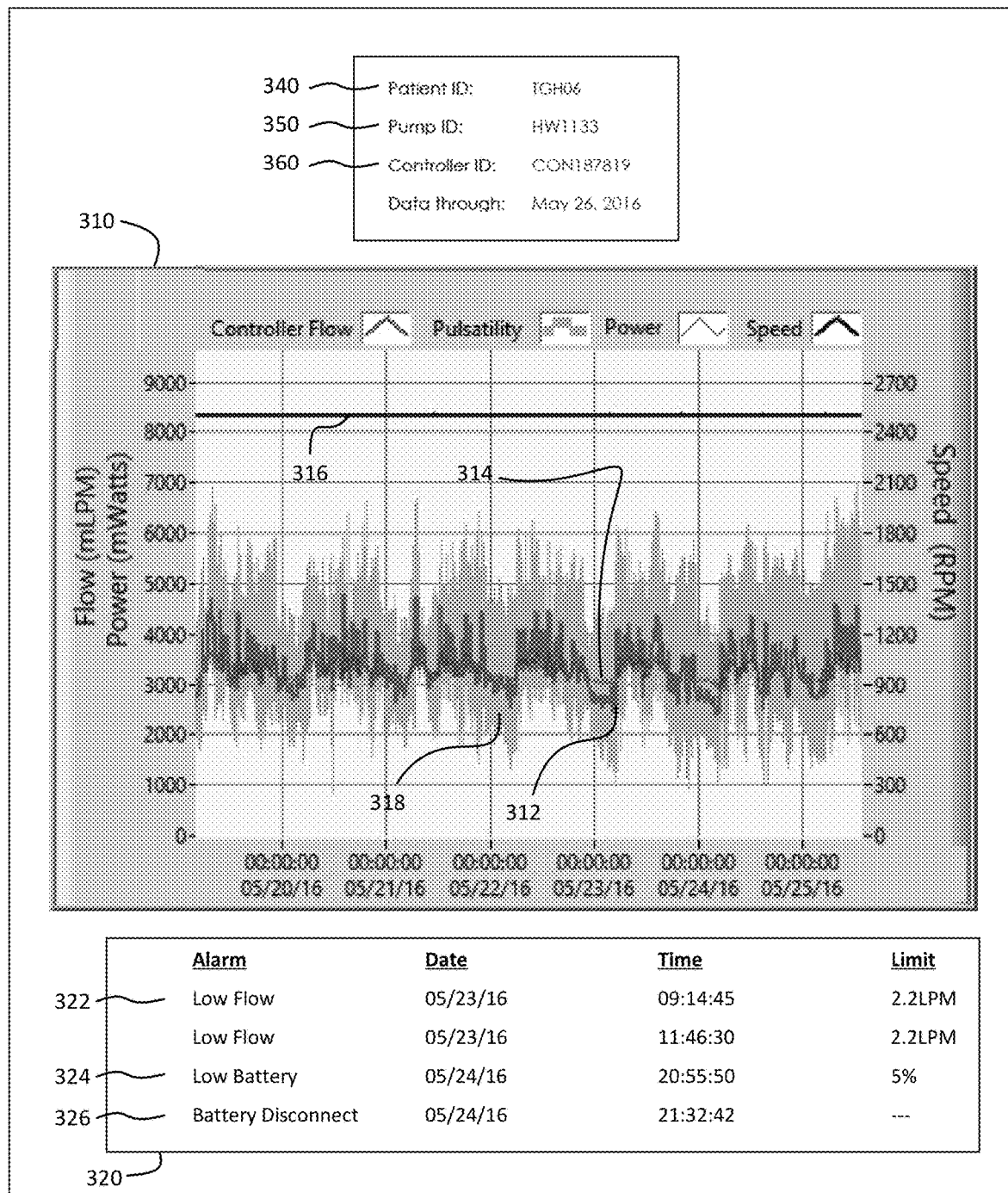
FIG. 3 an example of logged data from a VAD in a log file.

FIG. 3 shows an example of logged data 300 from a VAD. In the example of FIG. 3, the logged data 300 includes a flow rate of blood exiting the pump 312 (e.g., average flow), power supplied to the pump 314, motor speed of the pump 316, and flow pulsatility 318. These are examples of continuously logged data 310, since new data points are continuously logged for the duration of the VAD's operation. Other forms of continuously logged data include differential pressure exerted by the pump, parameters indicative of thrust on a rotor of the pump, or any other parameter from which operation of the pump may be estimated, measured, calculated or otherwise determined. These and other parameters are described in the following commonly owned and co-pending applications: U.S. application Ser. No. 13/355,297; U.S. application Ser. No. 14/950,467; U.S. Provisional Application Ser. No. 62/291,123. The disclosures of those applications are hereby incorporated by reference in their entireties.

The logged data 300 also includes event information (indicating physiological or operational events detected by the control circuit) and alarm information (resultant alarms issued by the control circuit). Low blood flow 322, high pressure, insipience presence or clearance of suction conditions, or adverse operating conditions of the device such as low battery 324 (either or both of internal and external batteries) and power disconnection 326, are examples of events that may result in issuance of an alarm. In such cases, both the event and the resultant alarm may be logged. Other events may not result in an alarm, such as a change in operational state of the pump (e.g., from continuous flow to pulsatile flow or vice versa, from synchronous flow to asynchronous or vice versa, from full-assist to partial assist). The events and alarms are examples of intermittently collected data 320, since over the duration of the VAD's operation, events and resultant alarms occur only intermittently.

In the example of FIG. 3, both continuously and intermittently collected data are associated with time stamps, such that the time of collection for a given data point may be identified using the time stamp. In FIG. 3, the timestamps of the continuously collected data 310 are illustrated in the form of a time-ordered waveform.

Optionally, the logged data 300 may also include any one or combination of information for identifying the patient (e.g., patient data 340), information for identifying the clinical device (e.g., device data 330, including model and device-specific identifications) and information for identifying the device controller (e.g., controller data 350, also including model and device-specific identifications). This data may be constant throughout operation of the pump and, therefore, not associated with a timestamp. This optional data may be included with the various logged data in the log file, or it may be stored separately. If stored separately, the optional data need not be extracted with the log file. The control circuit may include instructions indicating which types of data to transmit (e.g., logged data), and which types of data not to transmit (e.g., constant data), during a data extraction routine.

Figure 4:
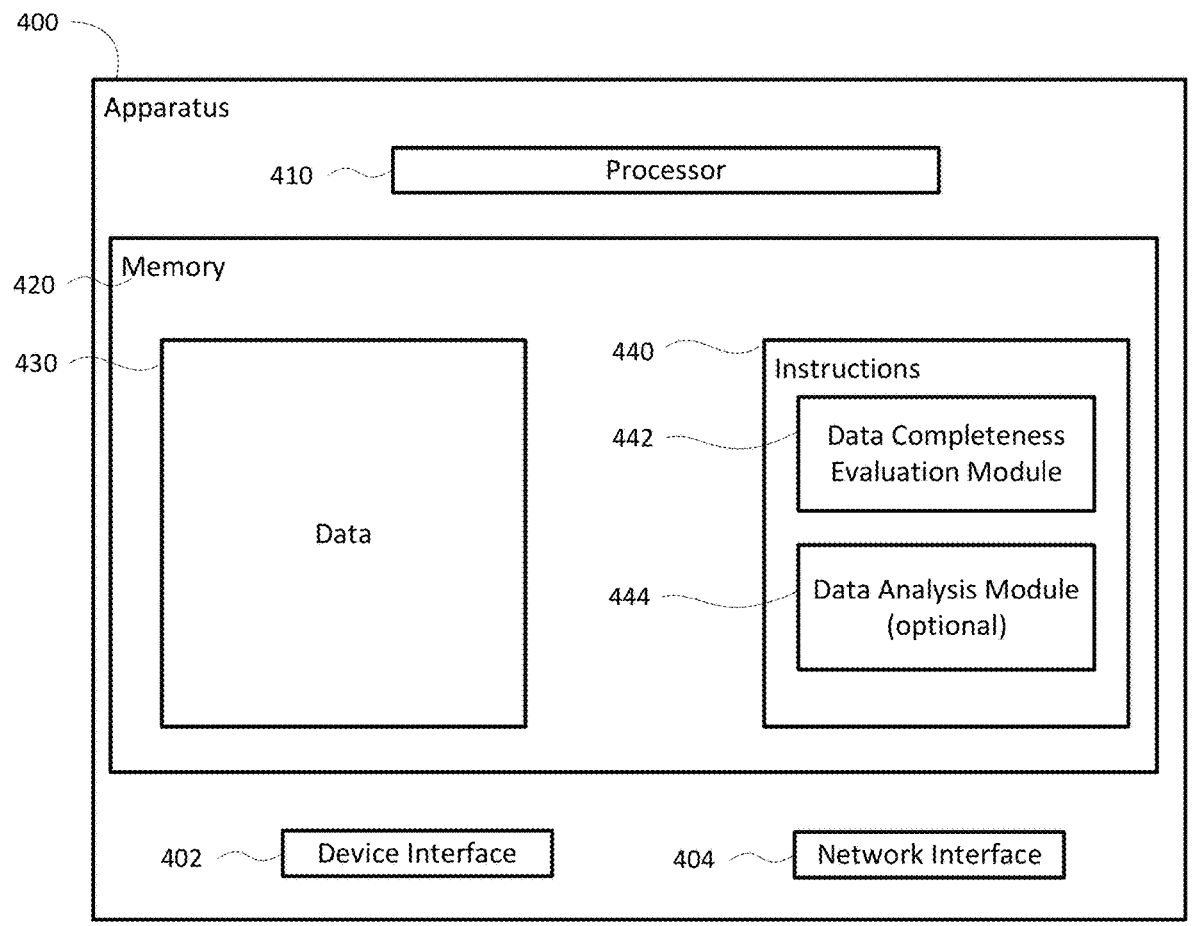
FIG. 4 is a block diagram of an example apparatus for extracting data from a clinical device.

FIG. 4 is a block diagram of an example apparatus 400 (e.g., the computer 120 of FIG. 1) for extracting data from a clinical device. The apparatus 400 includes a device interface 402 for connecting to the clinical device. As described above, the device interface 402 may be a wired or wireless connection. The apparatus 400 also includes a network interface 404, for instance for sending the extracted clinical data to a remote location over a network. As described above, the network interface 404 may also be a wired or wireless connection, or combination thereof.

The apparatus 400 further includes a processor 410 and memory 420. The processor 410 may be any standard processor, such as a central processing unit (CPU), or a dedicated processor, such as an application-specific integrated circuit (ASIC), a field programmable gate array (FPGA), a microprocessor, microcontroller containing memory, or other hardware that performs one or more operations. While one processor block is shown, the apparatus 400 may also include multiple processors which may or may not operate in parallel.

Memory 420 stores information accessible by processor 410 including instructions 440 for execution by the processor 410 and data 430 which is retrieved, manipulated or stored by the processor 410. The memory 420 may be of any type capable of storing information accessible by the processor, such as a DRAM, SRAM, FRAM, NVRAM, ROM, RAM, SDROM, hard-drive, ROM, RAM, CD-ROM, write-capable, read-only, or the like. Data 430 may include data received from a clinical device over the device interface 402, such as the data types described above in connection with FIGS. 2 and 3.

Instructions 440 may include a data completeness evaluation module 442 for determining completeness of the extracted data. For data included in a log file, determining completeness of the data may involve evaluating integrity of the received log file. The instructions may also optionally include a data analysis module 444 for analyzing the received data, so that the patient may be examined on site even before the data is transmitted to another location.

Figure 5:
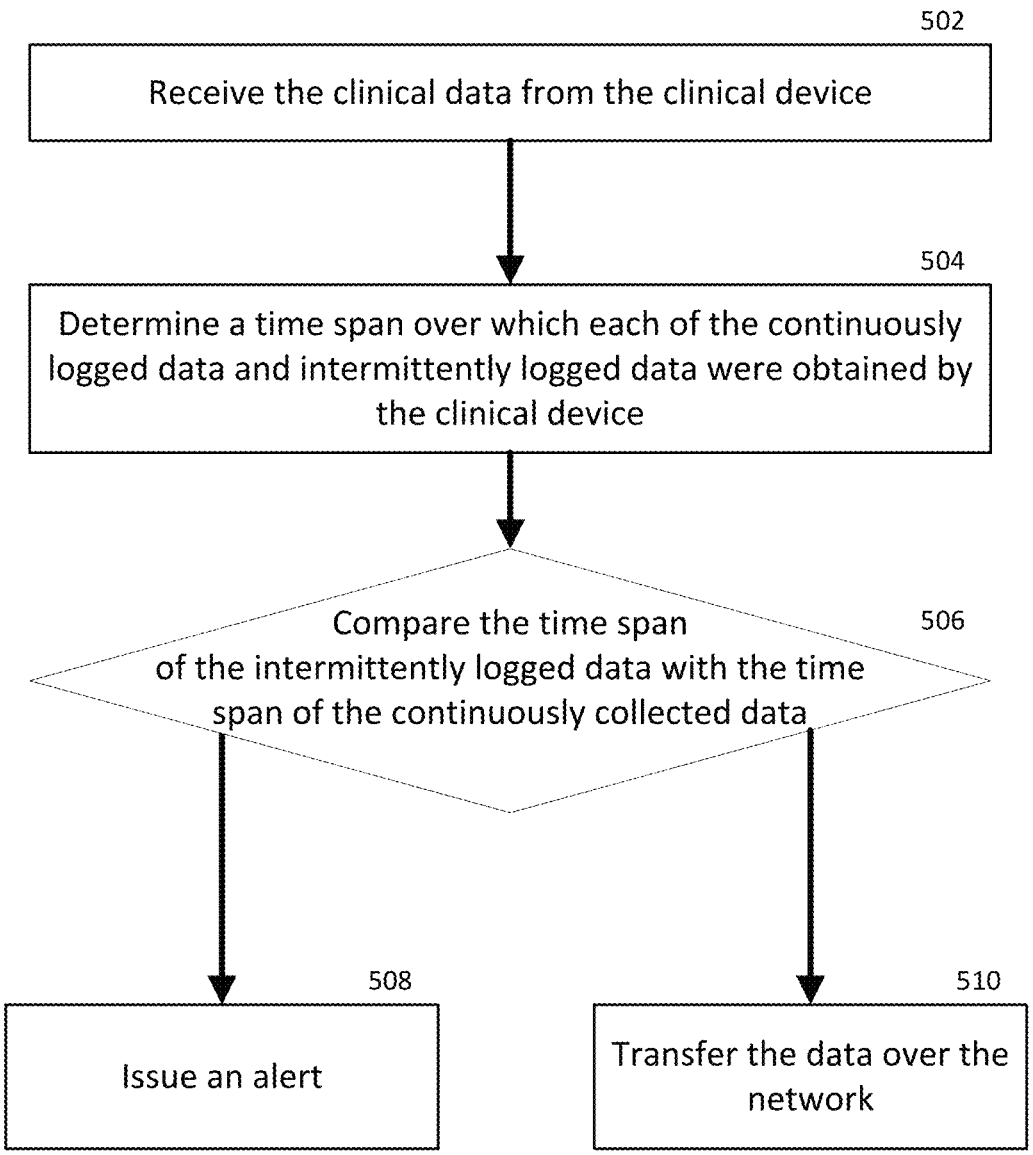
FIG. 5 is a flow chart of an exemplary method for extracting data from a clinical device.

The systems and devices described above may be operated using the example method operations described in FIG. 5. It should be understood that the following operations do not have to be performed in the precise order described below. Rather, various operations can be handled in a different order, or simultaneously. Moreover, operations may be added or omitted.

At 502, the apparatus receives data from a clinical device. The received data includes several types of data points, some of which are continuously logged (e.g., flow rate of blood exiting the pump, power supplied to the pump, motor speed of the pump, other operating parameters of the clinical device), and some of which are intermittently logged (e.g., low flow, suction condition, low battery, high power alarm, low power alarm, inflow or outflow occlusion, other events indicating change or adverse condition in operation of the clinical device). The received data also includes timestamps associated with the continuously logged and intermittently logged data points. Optionally, some of the received data may have been stored in the clinical device before the device began operating (e.g., patient information, pump information).

At 504, the apparatus determines a time span over which each of the continuously logged data and intermittently logged data were obtained. The time span may be determined using the timestamp data associated with each type of data. In one example, the time span may be starting and ending points in time, such as the timestamp of the earliest collected data point and the timestamp of the latest collected data point.

At 506, the apparatus compares the time span of the intermittently logged data with the time span of the continuously collected data. For example, the apparatus may identify the earliest and latest data points of the alarm data in a received data log and compare those timestamps with the time stamps of logged flow data of the data log. As a simplified example, if the alarm data indicates that a first alarm was triggered at 4 am, and that a last alarm was triggered at 9 am, but the first continuously logged flow data point was at 2 am and the last was at 6 am, comparing the data point time stamps will reveal that at least one hour of flow data (between 9 am and 10 am) is missing from the received data log. But if the last continuously logged flow data point were associated with a 10 am timestamp, it could be determined that the received data log is complete.

If multiple types of continuously logged data are extracted, the apparatus could additionally, or alternatively, compare the timestamps of one of the types of data with the timestamps of another in order to ensure that data collection for both types of data is indicated to have begun and ended at the same time. As an example, if the extracted data includes flow rate data points with timestamps ranging from 2 am to 6 am, and pump speed data points ranging from 2 am to 10 am, this may indicate that several hours of flow rate data were not properly extracted.

If it is determined that continuously collected data is missing from the received data log, then at 508 an alert may be issued. The alert may be automatically generated and provided to a user interface and may notify a person transferring the data from the clinical device to the apparatus to retransfer the data, since the initial transfer attempt ended prematurely. Automating this process negates the need for manual review of the data for completeness, either at the patient's location 101, or at another location 102. Otherwise, if there is no indication of missing data points, at 510, the data may be transferred from the apparatus over the network.

Alternative to the above examples, the time span may be a duration of time between the earliest and latest collected data points instead of the data points themselves. For instance, in the above example, it may be determined that the duration between the 4 am alarm and the 9 am alarm is 5 hours. The 5 hour duration may then be compared to the duration of collected flow data points. If that duration is 4 hours (from 4 am to 8 am), which is less than the duration of the alarm data, then it will be clear than some of the flow data is missing. But if the duration is 6 hours (4 am to 10 am), then there will be no indication of missing data and the data will be considered complete. Similarly, if the time duration for one type of continuously logged data does not equal the time duration for another type of continuously logged data, this too may indicate that the extracted data is incomplete.

While the above examples address comparisons between flow data and alarm data, it should be understood that the same or similar comparison may be made between any continuously logged data and any intermittently logged data. Similar comparisons may also be performed between two sets of continuously logged data. For instance, if both power data and flow data are received, and the time span of collection for one data set is greater than for the other, this too may be an indication of an incomplete data set.

In some examples, completeness of the data set is tested at the location of the patient, and the data is then transmitted to and analyzed elsewhere. However, in other examples of the disclosure, the apparatus at the location of the patient may perform an analysis of the data without having to send the data out. Alternatively, the apparatus at the location of the patient may be configured to send the data out over the network, and the apparatus receiving the data at the remote location may be configured to automatically check the received data for completeness. Such examples may similarly rely on the completeness-checking techniques described above.

Lastly, the above examples assume completeness of at least one data set that is compared. However, if every compared data set is incomplete, comparing the incomplete sets with one another may not reveal their incompleteness. In order to increase the likelihood of a complete data set being compared (or at least of not comparing two equally incomplete data sets), the various data transfers (e.g., extraction from the clinical device to the local computer, transmission from the local computer to the remote location) may be configured to first transmit one or some data sets in their entirely before beginning to transmit the remaining data set(s). For instance, it may be desirable to extract intermittently logged data first, and then to extract continuously logged data, in order to increase the likelihood of completeness of the intermittently logged data. For further instance, if there are multiple types of continuously logged data, it may be desirable to extract one type (e.g., flow rate data) in its entirety before beginning to extract another type (e.g., pump speed data).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended embodiments.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An automated method for evaluating completeness of data from a clinical device, the clinical data comprising continuously logged data, intermittently logged data including one or more logged alarms indicating a detected adverse operating condition of the clinical device, and timestamp data associated with the continuously logged data and intermittently logged data, the method comprising:
   receiving via a wireless interface over the air, a time-ordered waveform that includes the clinical data from the clinical device;
   extracting, via a processor, the timestamp data associated with the continuously logged data from the time-ordered waveform, the extracting including detecting occurrences of signal deviations in the received time-ordered waveform;
   determining a time span over which the continuously logged data was obtained based at least in part on the extracted timestamp data, the determining being based at least in part on determining an earliest data point of alarm data and a latest data point of alarm data, the earnest data point and latest data point being determined from the timestamp data;
   comparing the timestamp data associated with the intermittently logged data with the determined time span;
   comparing timestamps of different types of data to determine when the different types of data do not begin and end at a same time, the timestamps of different types of data being distinguishable by different signal deviations in the received time-ordered waveform; and
   when the time stamps of different types of data do not begin and end at a same time, then issuing an alert that at least one of the different types of data were not extracted.

2. The method of claim 1, wherein receiving the clinical data from the clinical device comprises receiving the intermittently logged data before receiving the continuously logged data.

3. The method of claim 1, wherein the continuously logged data comprises one or more operating parameters of the clinical device.

4. The method of claim 3, wherein the clinical device is a blood pump, and wherein the operating parameters of the blood pump comprises one or more of a flow rate of blood exiting the pump, power supplied to the pump, and motor speed of the pump.

5. The method of claim 1, wherein the intermittently logged data further comprises:
   one or more logged events indicating a change in operation of the clinical device.

6. The method of claim 5, wherein the clinical device is a blood pump, and wherein the intermittently logged data comprises at least one of:
   a low flow alarm;
   a suction condition alarm;
   a low battery alarm; and
   a power disconnection alarm.

7. The method of claim 1, wherein the clinical data further comprises patient data and clinical device data that are not associated with a timestamp.

8. The method of claim 1, wherein the clinical device is ventricular assist device or a blood pump.

9. The method of claim 1, wherein the recited steps are performed at a location of the clinical device, and further comprising, if all timestamp data associated with the intermittently logged data occurs within the determined time span, transmitting the clinical data over a network to a remote destination.

10. The method of claim 1, wherein the recited steps are performed at an originating location remote from the clinical device, and wherein the clinical data is received over a network connection from an originating location, and wherein the alert indicating that the continuously logged data of the clinical data is incomplete is transmitted over the network to the originating location.

11. An apparatus for evaluating completeness of clinical data being transferred from a clinical device, the clinical data comprising continuously logged data, intermittently logged data, and timestamp data associated with each of the continuously logged data and intermittently logged data including one or more logged alarms indicating a detected adverse operating condition of the clinical device, the apparatus comprising;
a wireless interface configured to wirelessly receive a time-ordered waveform that includes the clinical data from the clinical device; and processing circuitry configured to:
extract the timestamp data associated with the continuously logged data from the time-ordered waveform, the extracting including detecting occurrences of signal deviations in the received time-ordered waveform;
determine a time span over which the continuously logged data was obtained based at least in part on the extracted timestamp data, the determining being based at least in part on determining an earnest data point of alarm data and a latest data point of alarm data, the earnest data point and latest data point being determined from the timestamp data;
compare the timestamp data associated with the intermittently logged data with the determined time span;
compare timestamps of different types of data to determine when the different types of data do not begin and end at a same time, the timestamps of different types of data being distinguishable by different signal deviations in the received time-ordered waveform; and
when the time stamps of different types of data do not begin and end at a same time, then issue an alert that at least one of the different types of data were not extracted.

12. The apparatus of claim 11, wherein the processor is configured to determine whether the intermittently logged data is received before the continuously logged data.

13. The apparatus of claim 11, wherein the continuously logged data comprises one or more operating parameters of the clinical device.

14. The apparatus of claim 13, wherein the clinical device is a blood pump, and wherein the operating parameters of the blood pump comprises one or more of a flow rate of blood exiting the pump, power supplied to the pump, and motor speed of the pump.

15. The apparatus of claim 11, wherein the intermittently logged data further comprises:
one or more logged events indicating a change in operation of the clinical device.

16. The apparatus of claim 15, wherein the clinical device is a blood pump, and wherein the intermittently logged data comprises at least one of:
a low flow alarm;
a suction condition alarm;
a low battery alarm; and
a power disconnection alarm.

17. The apparatus of claim 11, wherein the clinical data further comprises patient data and clinical device data that are not associated with a timestamp.

18. The apparatus of claim 11, wherein the apparatus is located in proximity to the clinical device, and the processor is further configured to, if all timestamp data associated with the intermittently logged data occurs within the determined time span, transmit the clinical data over a network to a remote destination.

19. The apparatus of claim 11, wherein the apparatus is located remote from the clinical device, and wherein the apparatus receives the clinical data over a network connection from an originating location, and wherein the processor is further configured to transmit the alert indicating that the continuously logged data of the clinical data is incomplete over the network to the originating location.

* * * * *